(12) United States Patent
Kormann et al.

(10) Patent No.: US 6,926,603 B2
(45) Date of Patent: Aug. 9, 2005

(54) WITHDRAWAL OF SAMPLES

(75) Inventors: Georg Kormann, Homburg (DE); Werner Flohr, Kaiserslautern (DE)

(73) Assignee: Deere & Company, Moline, IL (US)

( * ) Notice: Subject to any disclaimer, the term of this patent is extended or adjusted under 35 U.S.C. 154(b) by 0 days.

(21) Appl. No.: 10/610,488

(22) Filed: Jun. 30, 2003

(65) Prior Publication Data

US 2004/0063478 A1 Apr. 1, 2004

(30) Foreign Application Priority Data

Jul. 6, 2002 (DE) .......................................... 102 30 475

(51) Int. Cl.[7] .............................. A01F 12/48; G01N 1/20
(52) U.S. Cl. ..................... 460/1; 460/114; 56/10.2 B; 56/51; 73/863.41; 73/863.91
(58) Field of Search .............................. 73/863, 863.41, 73/863.51, 863.52, 863.53, 863.56, 863.91, 863.92; 56/10.2 B, 51, 53; 460/1, 114, 115

(56) References Cited

U.S. PATENT DOCUMENTS

| 674,095 | A |   | 5/1901 | Overstrom |
|---|---|---|---|---|
| 2,295,437 | A | * | 9/1942 | Thompson ................ 73/863.23 |
| 3,006,367 | A | * | 10/1961 | Thompson et al. .......... 137/875 |
| 3,241,371 | A | * | 3/1966 | Horeth ..................... 73/863.23 |
| 4,026,154 | A |   | 5/1977 | Pfeiffer et al. ............. 73/423 R |
| 4,262,533 | A |   | 4/1981 | Jaeger ......................... 73/422 |
| 4,269,064 | A |   | 5/1981 | Johnson et al. ............... 73/422 |
| 4,663,978 | A |   | 5/1987 | Lenski et al. ................ 73/863 |
| 5,087,120 | A |   | 2/1992 | Anthony ..................... 356/36 |
| 5,212,994 | A |   | 5/1993 | von Alfthan et al. ......... 73/866 |
| 5,959,218 | A | * | 9/1999 | Strubbe ................... 73/861.73 |
| 6,119,531 | A | * | 9/2000 | Wendte et al. ........... 73/863.52 |
| 6,272,819 | B1 | * | 8/2001 | Wendte et al. ............... 56/11.9 |
| 6,327,899 | B1 | * | 12/2001 | Diekhans et al. .............. 73/73 |

FOREIGN PATENT DOCUMENTS

| DD |   | 8 972 | 1/1955 |
| DE | 41 25 228 | 2/1995 |
| DE | 197 44 485 | 4/1999 |
| EP | 0 908 086 | 9/1998 |
| FR | 2 801 380 | 5/2001 |
| WO | WO 85 04 957 | 11/1985 |
| WO | WO 89 10 548 | 11/1989 |
| WO | WO 90 07 110 | 6/1990 |

* cited by examiner

Primary Examiner—Robert E. Pezzuto
Assistant Examiner—Nathan S Mammen

(57) ABSTRACT

An arrangement for the withdrawal of samples from a flow of harvested crop flowing in a conveying channel in a harvesting machine includes a guide element mounted so as to cover a sample withdrawal opening provided in a wall of the channel. The guide element is mounted for movement between a first position wherein it blocks the withdrawal opening, and in a second position wherein it opens the withdrawal opening and includes a region that is inserted into the conveying channel so as to forcibly deflect a crop sample through the withdrawal opening.

6 Claims, 2 Drawing Sheets

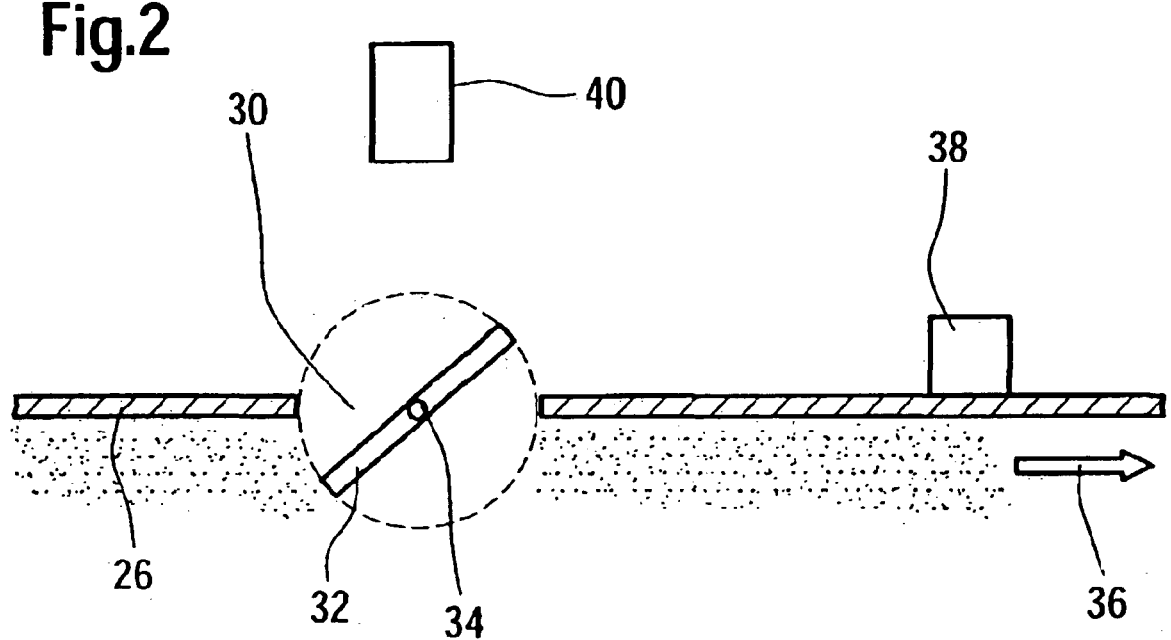
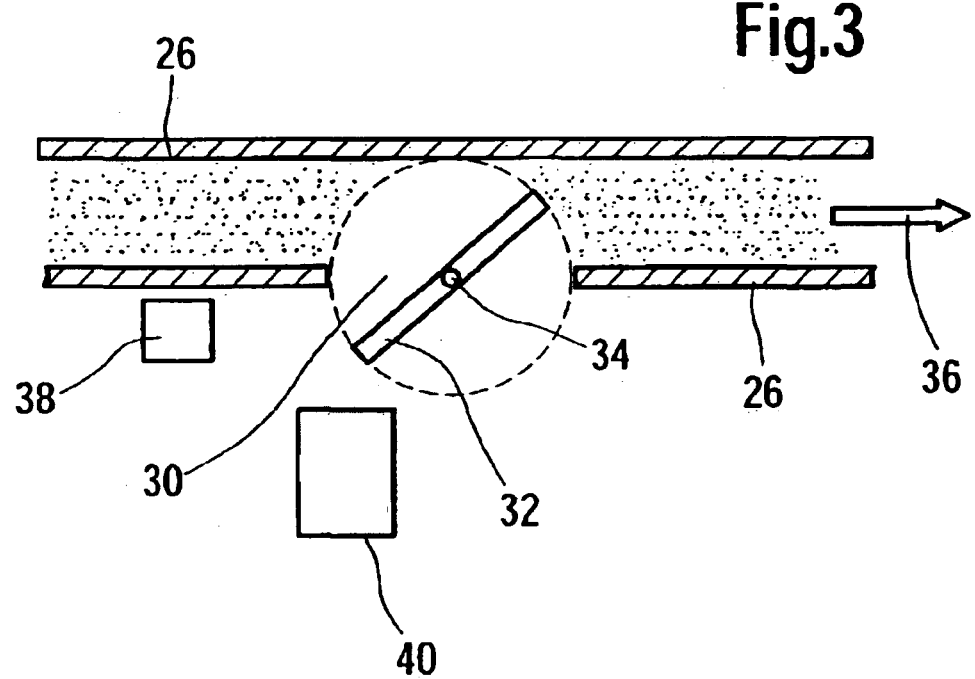

WITHDRAWAL OF SAMPLES

FIELD OF THE INVENTION

The invention concerns an arrangement for the withdrawal of samples from a flow of harvested crop flowing in a conveying channel in a harvesting machine.

BACKGROUND OF THE INVENTION

In agriculture, there is an interest in obtaining information about quality parameters of harvested crop. Several parameters of the harvested crop can already be detected during the harvesting process, such as moisture, as is described, for example, by EP 0 908 086 A on the basis of a combine. For the determination of some other parameters of the harvested crop, such as the percentage of amylum, the withdrawal of samples for later analysis in a laboratory is useful. Here an automation is desirable.

FR 2 801 380 A describes an automatic sample withdrawal arrangement for a combine. In the grain elevator, an opening is provided that can be repositioned and closed through which grain trickles to a conveyor that fills it into a hose. By clamping off sections of the hose, individual samples are generated, the location of whose origin can be detected by a satellite-supported position detection system. Information regarding the position and the number of the sample is stored in a data bank for later identification.

According to the disclosures of EP 0 908 086 A and FR 2 801 380 A, one part of a flow of crop trickles through an opening and is then collected until a sufficient amount is available as a sample. Since the sample is taken out of the crop flow on the basis of its gravity, problems can occur when the crop contains a high degree of moisture. For example, the withdrawal of silage from the flow of the crop of a forage harvester can not successfully be accomplished using these solutions.

SUMMARY OF THE INVENTION

The problem underlying the invention is seen in the need for an improved sample withdrawal arrangement.

An object of the invention is to provide an arrangement for withdrawing a sample from a stream of harvested crop by selectively inserting a guide or deflector into the stream so as to cause a sample of the crop to move to a collection station.

In this way a region of the guide element is inserted into the flow of the crop with the result that the harvested crop is forced to deflect. The resulting jam provides the assurance that harvested crop is actually withdrawn from the conveying channel. An appropriate selection of the size of the guide element can provide the assurance that a representative sample of the entire cross section of the flow of the harvested crop can be withdrawn.

One solution is to attach the guide element so that it can pivot freely. Thereby, it can be moved between a sample withdrawal position and a non-operating position. In the non-operating position, it preferably closes an opening in a wall of the conveying channel, so that an undisturbed flow of the harvested crop is possible. In the sample withdrawal position, it frees the opening, and a region of the guide element extends into the flow of the harvested crop. The deflected flow of the harvested crop as a rule then flows through the opening. The pivot axis of the guide element extends appropriately at least approximately transverse to the direction of the flow of the crop. Embodiments are also conceivable with a (exclusively or additionally) movable guide element that can be slid into the conveying channel and slid out of it again.

Fundamentally, it would be conceivable to attach the guide element to the wall of the conveying channel, pivoted at one end. However, the arrangement of the pivot axis approximately at the center of the guide element (relative to the direction of flow of the crop in the conveying channel) is particularly appropriate. Thereby, the guide element can be used from two sides. If one side is worn after prolonged use, the guide element can be turned, or both sides are used alternately and thereby wear-life is extended. Furthermore, there is the possibility of using a rotary drive with a single direction of rotation.

There are various possibilities regarding the positioning of the region of the guide element that can be inserted into the conveying channel. In a first embodiment, this region is arranged at an angle of less than 90° to the direction of flow of the crop. With a guide element that can be pivoted, it is then arranged upstream of the pivot axis of the guide element. Thereby the crop maintains its direction of flow, at least approximately, even when the guide element is in the sample withdrawal position. It is, however, deflected through a certain angle. In another embodiment, the region of the guide element extending into the conveying channel in the sample withdrawal position is oriented transverse to the direction of flow of the harvested crop, or the angle between the guide element and the direction of flow is even greater than 90°. In the case of a guide element that can be pivoted, the aforementioned region is then located downstream of the pivot axis of the guide element. A jam of the harvested crop then develops that leads to the crop reaching out of the conveying channel for the withdrawal of the sample.

In order to withdraw a greater number of samples on larger fields, an automation of the sample withdrawal process is a solution. For this purpose, a drive for the pivoting of the guide element about its pivot axis driven by outside force and an appropriate means for inserting the sample of the harvested crop withdrawn from the flow of the crop into a sample container are appropriate. An appropriate control arrangement controls the drive that brings about the insertion of the guide element into the conveying channel on the basis of a manual input or when pre-determined points in time and/or locality are passed, at which the guide element is pivoted. The harvested crop that, was withdrawn reaches a sample container by means of a conveyor or its own kinetic energy. The actual position of the guide element can be monitored by appropriate sensors. These provide assurance that the sample was actually taken and that the guide element is subsequently returned to its non-operating position.

Preferably, information is stored, for example, in a data bank on the basis of which the particular sample container can later be identified. For example, a printing of the sample container with corresponding information is conceivable, such as, for example, a bar code or the storing of the information in a transponder connected to the container. It would also be conceivable to store a sample container number or information about the position at which the sample container is located in a data bank. Also, the origin of the location at which the sample was taken may be determined by a position detection system—preferably satellite supported—(or another magnitude on the basis of which the sample can later be identified, such as the time of its generation) can be stored in memory or imprinted on the sample container. Instead of storing the sample in a sample container and to analyze it later in a laboratory, an on-thespot analysis by means of appropriate implements would also be possible.

The invention is appropriate for any harvesting machine in which the harvested crop flows through a conveying channel, for example, balers, self-loading forage boxes, combines or forage harvesters. In the case of the latter, the guide arrangement is preferably arranged in the discharge duct.

BRIEF DESCRIPTION OF THE DRAWINGS

The drawing shows two embodiments of the invention that shall be described in greater detail in the following.

FIG. 2 shows the discharge duct of the harvesting machine incorporating a first embodiment of a guide element for the withdrawal of a sample from the duct.

FIG. 3 shows the discharge duct of the harvesting machine incorporating a second embodiment of a guide element attached to it for the withdrawal of a sample.

DESCRIPTION OF THE PREFERRED EMBODIMENT

Figure 1:
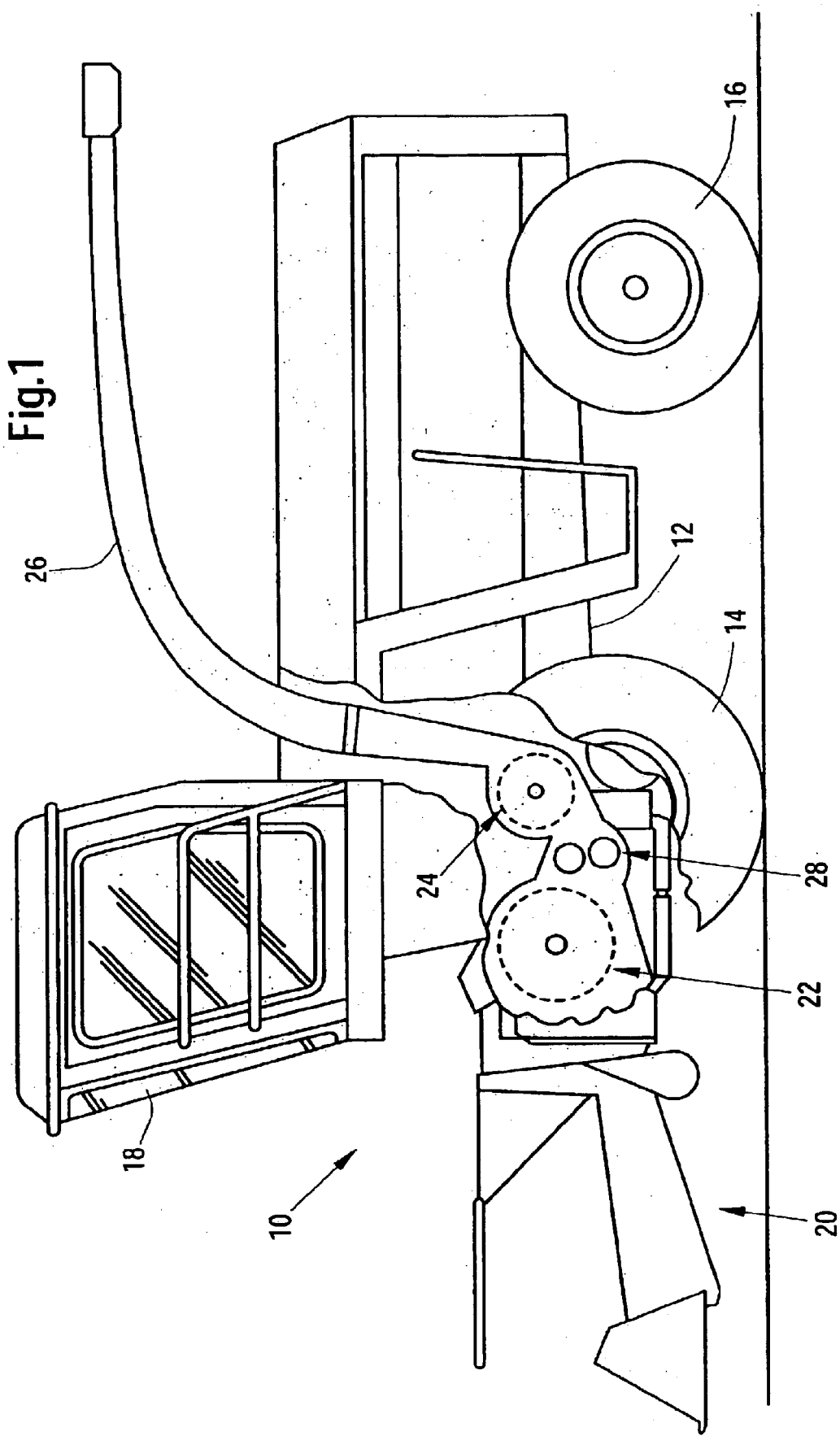
FIG. 1 shows a schematic left side view of a harvesting machine of the type with which the invention is useful.

Referring now to FIG. 1, there is shown a harvesting machine 10, in the form of a self-propelled forage harvester, supported on a frame 12 that is carried by front and rear wheels 14 and 16. The harvesting machine 10 is controlled from an operator's cab 18 from which a crop take-up arrangement 20 can be controlled while being within view of the operator. Crop, for example, corn, grass, or the like, taken up from the ground by means of the crop take-up arrangement 20 is conducted to a chopper drum 22 that chops it into small pieces and delivers it to a conveyor arrangement 24. The crop leaves the harvesting machine 10 to an accompanying trailer through a discharge duct 26 that is mounted for swinging about an upright pivot axis. A post-chopper reduction arrangement or kernel processor 28 is located between the chopper drum 22 and the conveyor arrangement 24 through which the crop to be conveyed is conducted tangentially to the conveyor arrangement 24.

FIG. 2 shows a vertical section along the discharge duct 26. An opening 30 is provided in the upper wall of the discharge duct 26. Within the opening 30, a guide element 32 is located that takes the form of a flat sheet metal plate that is supported in bearings so as to pivot about a pivot axis 34 extending horizontally and transverse to the plane of the drawing. In plan view, the guide element 32 may be circular or rectangular in shape. Relative to the direction of the flow of the crop, that is indicated by the arrow 36, the pivot axis extends through the center of the guide element 32. A drive 38, actuated by outside force, in the form of an electric or hydraulic motor using transmission elements, not shown, selectively causes a rotation of the guide element 32 about the pivot axis 34. FIG. 2 shows the guide element 32 in its sample withdrawal position in which the harvested crop flowing through the discharge duct 26 impinges upon the region of the guide element 32 at an angle of approximately 45°, which region is located (relative to the flow of the crop) upstream of the pivot axis 34. Crop which impinges on this region of the guide element 32 is deflected upward by the guide element 32, so that it reaches a sample container 40. The guide element 32 can be brought into a non-operating position, by the drive 38, in which it extends parallel to the adjoining wall of the discharge duct 26 and closes the opening 30. The sample container 40 may be, for example, a bottle, a paper bag or a box. The sample container 40 is extracted from a magazine by an arrangement, not shown, for example, a gripping arm, and is returned to the magazine after being filled with the sample of the harvested crop. An electronic control assigns a place for the sample container 40 in the magazine, for correspondence to that location at which the sample was taken, for later evaluation. The use of a hose as suggested in FR 2 801 380 A would also be conceivable for the retention of the sample.

FIG. 3 shows a second embodiment of a guide element 32. Elements corresponding to those of the first embodiment are given the same number call-outs. However, FIG. 3 shows a horizontal section along the discharge duct 26. The discharge duct includes the two side walls shown in FIG. 1. In one of these, the opening 30 is provided for the guide element 32, that can pivot about the pivot axis 34 extending vertically. In the sample withdrawal position shown, the region of the guide element 32, extending into the interior of the discharge duct 26, is arranged downstream of the pivot axis 34 relative to the flow of the harvested crop. The harvested crop impinges upon the guide element 32 at an angle of approximately 135°. Here, a back-draft develops that results in the harvested crop reaching the sample container 40. In this embodiment, the drive 38 is also arranged to bring the guide element 32 into a non-operating position, in which it extends parallel to an adjoining wall of the discharge duct 26 and closes the opening 30.

The arrangement, according to the invention shown here, makes it possible to withdraw samples automatically from the discharge duct 26 of the harvesting machine 10 that takes the form of a forage harvester. These samples are fundamentally important for the development of calibrations of NIR measurement systems. Furthermore a GEO-referenced sample withdrawal of test strips is possible during the harvest. In addition, the owner is offered the possibility of checking the accuracy of a moisture content measuring system or a control system for quality parameters of the harvested crop and, if necessary, to calibrate these anew.

Having described the preferred embodiment, it will become apparent that various modifications can be made without departing from the scope of the invention as defined in the accompanying claims.

What is claimed is:

1. Arrangement for the withdrawal of samples from a flow of harvested crop flowing in a conveying channel of a harvesting machine in a direction of flow toward a discharge end of said conveying channel, comprising: said conveying channel being provided with a wall containing an opening through which crop samples may be withdrawn; said opening being symmetrical about a central axis disposed in alignment with said wall; a guide element having a shape complementary to said opening and being mounted to said conveying channel for pivotal movement about said axis between a sample withdrawal position in which it frees said opening for permitting a crop sample to move through, and in which it projects into said channel so as deflect crop through, said opening, and a closed position, wherein said guide element is located within and blocks said opening so as to prevent crop from moving through said opening.

2. The arrangement, as defined in claim 1, wherein said central axis extends at least approximately transverse to said direction of flow of crop.

3. The arrangement, as defined in claim 1, wherein said region of said guide element extending into the conveying channel is inclined, when in the sample withdrawal position relative to the direction of flow of the harvested crop by one of less than 90° and more than 90°.

4. The arrangement, as defined in claim 1, and further including a drive coupled to said guide element for selectively pivoting said guide element about said central axis.

5. The arrangement, as defined in claim 1, wherein said conveying channel is defined by a discharge spout of a forage harvester.

6. Arrangement for the withdrawal of samples from the flow of harvested crop flowing in a conveying channel of a harvesting machine in a direction of flow toward a discharge end of said conveying channel, comprising: said conveying channel being provided with a wall containing an opening through which crop samples may be withdrawn; said opening being symmetrical about a central axis; a guide element having a shape complementary to said opening and being mounted to said conveying channel for pivotal movement about said axis between a sample withdrawal position in which it frees said opening for permitting a crop sample to move through, and in which it projects into said channel so as deflect crop through, said opening, and a closed position, wherein said guide element is located within and blocks said opening so as to prevent crop from moving through said opening; and said opening being so located relative to said direction of flow of crop and said guide element that said guide element projects downstream within said conveying channel and said crop runs through said opening in said wall when the guide element is brought into said sample withdrawal position.

* * * * *